United States Patent [19]

Lecloux et al.

[11] 4,125,543

[45] Nov. 14, 1978

[54] PROCESS FOR PREPARING EPOXIDES

[75] Inventors: André Lecloux; Michel Köhler; Paul Dantinne, all of Brussels, Belgium

[73] Assignee: Interox, Brussels, Belgium

[21] Appl. No.: 754,318

[22] Filed: Dec. 27, 1976

[30] Foreign Application Priority Data

Jan. 9, 1976 [LU] Luxembourg ............................ 74148

[51] Int. Cl.$^2$ ........................................... C07D 301/14
[52] U.S. Cl. ............................................... 260/348.25
[58] Field of Search ..................... 260/348.5 L, 348.25

[56] References Cited

U.S. PATENT DOCUMENTS 2,976,265  3/1961  Pearce ........................... 260/348.5 L

OTHER PUBLICATIONS

Toru Takagi, Journal of Applied Polymer Science, vol. 19 (1975) pp. 1649–1662.

*Primary Examiner*—Norma S. Milestone
*Attorney, Agent, or Firm*—Larson, Taylor and Hinds

[57] ABSTRACT

The invention concerns a process for the preparation of epoxides by reaction of olefins with a percarboxylic resin. The percarboxylic resins are washed with a solvent containing water before being brought in contact with the olefins.

16 Claims, 1 Drawing Figure

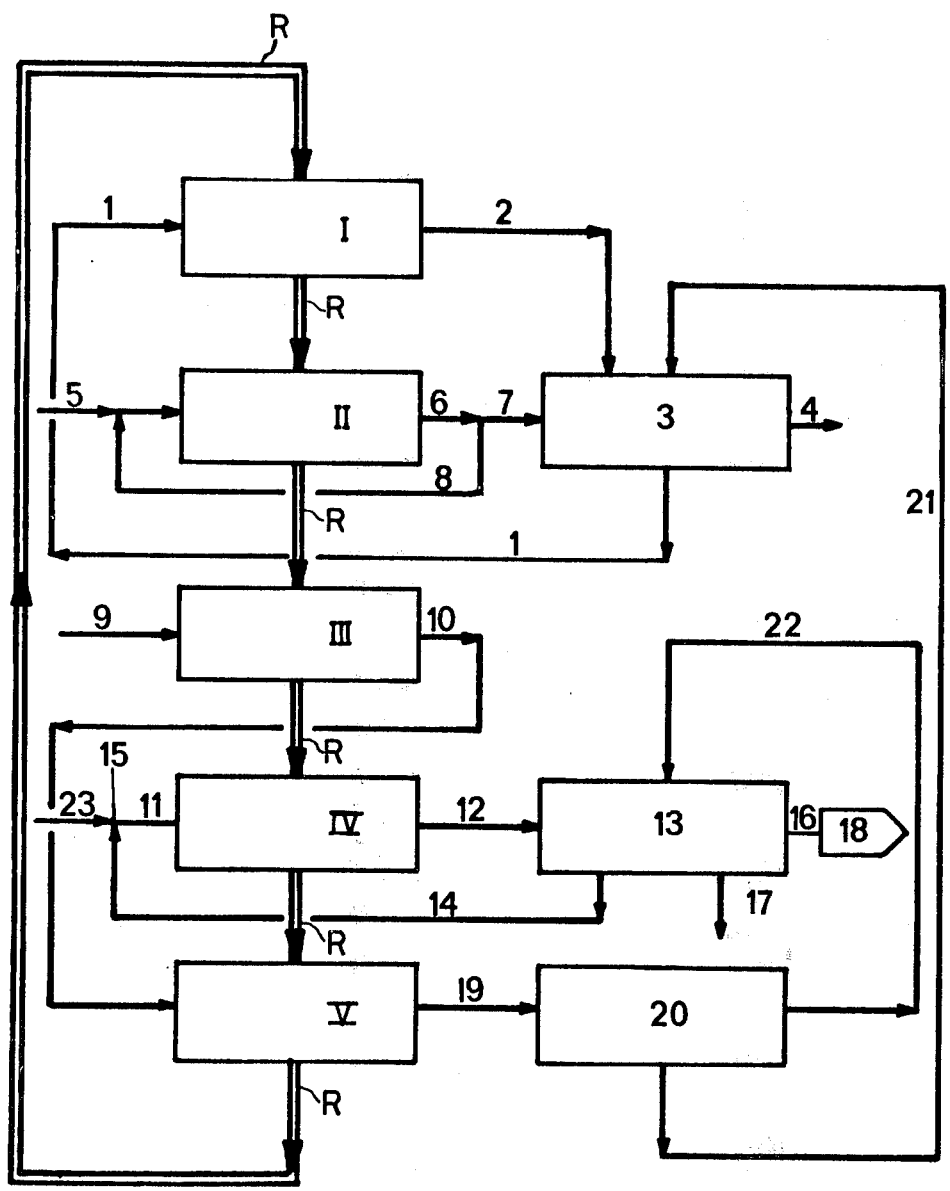

PROCESS FOR PREPARING EPOXIDES

The present invention concerns a process for the preparation of epoxides by epoxidation of substituted or unsubstituted olefins or cycloolefins by means of peroxy compounds.

The preparation of epoxides is usually done with a peracid that is reacted with the olefin to be epoxidised. Peracids such as peracetic acid and performic acid are often used for this purpose.

It has recently been suggested that very special polymeric peracids (J.Appl.Pol.Science, 1975, 19 pp 1649–1662) be used. These resins are prepared by reaction of polymers bearing carboxy functional groups with hydrogen peroxide in an acid medium. Before being used at the epoxidation stage the peroxidised resin obtained is washed with methanol until the acid and the hydrogen peroxide not used up by the reaction are completely removed. According to this process it is equally possible to envisage washing with the solvent used for the epoxidation reaction : dioxane, ethanol, isopropanol or tert-butanol.

The peroxidised resins have until now been used to oxidise cyclic olefins, olefins substituted by aromatic groups, or long-chain olefins.

One disadvantage of their use according to the known process is the formation of by-products, mainly glycols, in large quantities. In the epoxidation of light olefins this formation of by-products is so large that hardly any epoxide is obtained. Such is the case for example with propylene.

The applicant has now found a process for epoxidising olefins that does not have this disadvantage.

The present invention therefore concerns a process for the preparation of epoxides by reacting olefins with peroxidised carboxylic resins in which process the peroxidised resins are washed with a solvent containing water before being put into contact with the olefins.

The solvent used is preferably pure water. However, it is equally possible to use mixtures of water with one or more polar solvents miscible with water and inert vis-à-vis the peroxidised resin in the working conditions, such as notably cyclic or aliphatic ethers and esters. As cyclic ethers there are generally used ethers containing 5 to 6 atoms in the ring of which 1 to 3 atoms are oxygen and the carbon atoms of which may possibly be substituted by alkyl groups containing 1 to 3 carbon atoms. The aliphatic ethers generally contain 2 to 12 and preferably 4 to 10 carbon atoms and 1 to 3 oxygen atoms. The esters generally contain 2 to 12 carbon atoms. Water-dioxane and water-tetrahydrofuran mixtures are well suited. In the mixtures of water with one or more polar solvents, the water content may vary; however, it is most often at least 40% by weight of the mixture.

The quantity of solvent used for washing may vary in very wide limits and is not critical. It is however necessary to see that a sufficient quantity is used so that the solvent coming from washing does not contain more than a few products which were adsorbed on the peroxidised resin, such as solvents, reagents or by-products originating from its preparation. The excess solvent may afterwards be removed by any known process such as filtration, drying etc. Other processes may be equally suitable. The resin can then be dried by any known process such as vacuum evaporation, drying in a fluidised bed etc. Other processes may be equally suitable.

In general, it is possible to use a peroxidised resin still containing a certain quantity of adsorbed solvent and it is preferable not to dry the resin too much. Indeed, although the selectivity of the reaction does not depend on the quantity of the solvent, according to the invention, adsorbed on the peroxidised resin it will however be noted that the rate of epoxidation increases when the quantity of solvent adsorbed increases. Therefore, in order to optimise the economy of the process, it is preferable to use peroxidised resins still containing at least 0.1% by weight solvent. In practice, peroxidised resins are used directly, containing a quantity of adsorbed solvent near the maximum quantity that can be adsorbed, obtained after washing and brief separation of the solvent by filtration and/or drying.

The washing temperature can vary; it is of course between the freezing temperature of the solvent and the decomposition temperature of the peroxidised resin. Usually temperatures between 0° and 80° C. are used.

The washing operation can be effected in any known way. The peroxidised resin can be placed on a filter and washed using the solvent; it is equally possible to place the resin in a column in which the solvent flows. Other processes are of course equally suitable.

Washing using the solvent according to the invention is preferably carried out immediately on the peroxidised resin obtained by peroxidation of a resin containing carboxy groups. It is however equally possible to carry out washing using the solvent according to the invention of a peroxidised resin prepared in advance and stored. This second possibility is however less favourable as it necessitates storing a product which is likely to decompose with the risk of explosion if it is dry, or likely to lose its active oxygen.

The peroxidised resins used in the process according to the invention are obtained by any known process. In general, a resin containing carboxy groups is reacted with a solution of hydrogen peroxide at variable temperatures lower than the decomposition temperature of the peroxidised resin. These temperatures are generally between 0° and 80° C. and preferably between 10° and 60° C. The reaction takes place preferably in the presence of an acid catalyst.

Various types of solution of hydrogen peroxide may be used. Generally, solutions of hydrogen peroxide in water are used. The concentrations of hydrogen peroxide in aqueous solution are variable. Often, a reaction mixture containing 5 to 65% by weight hydrogen peroxide is used. The grades of hydrogen peroxide used for this purpose must often have a hydrogen peroxide content between 20 and 85% by weight. The quantity of hydrogen peroxide used depends on the number of carboxyl functional groups present in the resin. In general, quantities of hydrogen peroxide are used that are equal to or greater than the quantities necessary to peroxidise all the carboxy functional groups of the resins. It is possible to use an excess of hydrogen peroxide inasmuch as the hydrogen peroxide not used up can be recirculated to the process. It is equally possible to use the hydrogen peroxide in near-stoichiometric quantities.

The acidity of the peroxidation medium is assured by the presence of a strong acid such as, for example, sulphuric acid, nitric acid, phosphoric acid and sulphonic acids such as para-toluenesulphonic acid, methanesulphonic acid, benzenesulphonic acid and benzylsulphonic acid. Other strong acids not modifying the resin in any other way may be equally suitable. The acid concentration in the reaction mixture is variable. It will however be necessary to see that excessively high concentrations are not used in order to avoid the possible degradation of resins that can be observed with certain acids. Excessively weak concentrations, without being troublesome, can however be disadvantageous in that they yield, after rather long times, resins with a low active oxygen content. Usually, the acid normality of the reaction mixture is between 0.5 and 20.

The resin peroxidation stage can take place in very different types of apparatus well known in themselves. It is possible to place the resin into a column in which there is a continuous flow of an acid solution of hydrogen peroxide. It is equally possible to introduce successively into the column containing the resin an acid solution and afterwards a solution of hydrogen peroxide. Another process consists of putting the resin in suspension in the acid solution of hydrogen peroxide into a vessel provided with stirrers. Other types of apparatus may be equally suitable. Continuous or discontinuous operation is possible.

The resins used to prepare peroxidised resins used in the process according to the invention are resins containing carboxy functional groups—COOH.

It is preferable to use carboxylic resins which in the peroxide state do not dissolve in the washing solvent. By this is meant that at least 95% of the peroxidised carboxylic resin does not dissolve during the washing stage in the washing conditions.

Various types of polymers may be used for this purpose. Examples of polymers that can be particularly suitable are those containing, notably, identical or different monomeric units of the formula

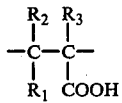

where $R_1$ and $R_3$ represent a hydrogen atom, a halogen atom, a hydroxyl group, a carboxy group, an aryl group substituted or unsubstituted by a halogen, a hydroxyl group or an alkyl group containing 1 to 3 carbon atoms, or an alkyl group substituted or unsubstituted by a halogen, a hydroxyl group or a carboxy group and containing 1 to 5 carbon atoms, $R_1$ and $R_3$ being either identical or different and where $R_2$ represents a hydrogen atom or an alkyl group-substituted or unsubstituted by a halogen, a hydroxyl group or a carboxy group and containing 1 to 5 carbon atoms.

The resins used in the preparation of peroxidised resins suitable for carrying out the process according to the invention can be homopolymers, copolymers or graft polymers containing monomeric units such as those defined above. Amongst the copolymers that can be used, apart from those containing different monomeric units such as those defined above, are those also containing monomeric units of the vinyl type substituted by aromatic groups such as those derived from styrene and its compounds like sodium styrene-sulphonate, divinylbenzene and alpha-methylstyrene for example, or monomeric units of the vinyl type substituted by hydroxyl, hydroxyalkyl, formyl, nitrile, acetoxy, acetoxymethyl, carbamyl, N,N-dialkylcarbamyl or 2-oxopyrrolidin-1-yl groups. Amongst the graft polymers that can be used are notably the vinyl polymers grafted by monomeric units such as those defined above.

Amongst these resins, homopolymers, copolymers and graft polymers of acrylic acids and methacrylic acids as well as hydrocarboxylated polymers such as the polymers described in German Patent Application No. 1,904,940 filed on Feb. 1, 1969 in the name of Degussa, substituted or unsubstituted poly-alpha-hydroxyacrylic acids and their copolymers, all these derivatives being possibly used in their lactonised form, are well suited. Polymers, copolymers and cross-linked polymers containing monomeric units derived from acrylic and methacrylic acids, insoluble in the peroxidation medium, have proved to be interesting to use. The copolymers of acrylic acid or methacrylic acid with olefins are well suited. These products are notably decribed in Encyclopaedia of Polymer of Science and Technology of H. Mark and collaborators, Vol. 7, p. 690 et seq. Interscience 1967.

Other derivatives containing carboxy groups are equally suitable. In general, polymers are used of which at least 1 and preferably 20% of the monomeric units contain a carboxyl functional group. The number of carboxyl functional groups present on the resin is not however critical.

The molar mass of carboxylic resins to be peroxidised is very variable; it can be between 1,000 and 1,000,000. It will however be necessary to see that the molar mass of the resin is sufficient for the resin, once peroxidised, to be insoluble or slightly soluble in the washing solvent.

The resins used for preparing peroxidised resins most often have a lower polarity than that of the solvent used for the epoxidation reaction. These solvents are defined below.

The peroxidised resin, once washed according to process of the invention, are reacted with olefins according to any process known in itself.

The olefins that can be epoxidised according to the process that is the subject of the present invention are chosen amongst substituted or unsubstituted linear or cyclic olefins. These olefins generally contain 2 to 20 carbon atoms. They may contain one or more double bonds. They may be substituted by various functional groups such as for example hydroxyl, alkoxyl, alkyl, cycloalkyl, or aryl groups or by halogen atoms. The process is particularly suitable for the epoxidation of $C_3$–$C_8$ olefins such as for example, propylene, allyl chloride, allyl alcohol, butenes-1 and -2, butadiene, 2-butene-1,4-diol, vinylcyclohexene and styrene.

The epoxidation reaction is effected by putting the gaseous or liquid olefin in contact with the peroxidised resin in the presence or absence of a solvent. When the olefin is present in gaseous form in the reaction conditions, a solvent is used in order to improve the transfer of the olefin towards the resin. When the olefin is liquid, the reaction can be effected in the absence of a solvent. However a solvent is most often used for epoxidation. This epoxidation solvent is chosen amongst the solvents that do not substantially solubilise peroxidised resins. On the other hand, it must solubilise at least partially the olefins to be epoxidised. Furthermore, it must be inert in epoxidation conditions vis-à-vis the peroxidised resin and the olefin. The polar solvents have proved to be particularly suitable for the epoxidation stage. Generally, a solvent is used whose polarity is equal to or greater than that of the resin.

Solvents particularly suitable for epoxidation are: aliphatic or cyclic ethers, such as monoglyme (monomethylether of diethylene glycol), diglyme, methoxyethane, dimethoxyethane, dioxane, tetrahydrofuran or trioxane for example, esters such as methyl acetate, epoxides such as the reaction products themselves, water and their mixtures. However other solvents may be equally suitable. Water in a mixture with dioxane or tetrahydrofuran is particularly suitable.

The temperature at which oxidation takes place does not exceed the decomposition temperature of the peroxidised resins. It is usually between 0° and 80° C. and preferably between 10° and 70° C. Epoxidation pressures may be equal to, lower than or greater than atmospheric pressure. They are usually between 0.8 and 30 kg/cm$^2$. When the olefins are gaseous at the reaction temperature, it is however preferable to use pressures greater than atmospheric pressure, generally between 2 and 30 kg/cm$^2$ in order to increase the concentration of the olefin in the solvent. Greater pressures however may be used when the solubility of the olefin in the solvent is poor.

The quantity of the olefin used may be equal to, greater than or less than the stoichiometric quantity corresponding to active oxygen content of the peroxidised resin. For reasons of economy, it is however preferable to use an excess, sometimes very large, of olefin in order to exhaust the peroxidised resin in active oxygen. The unconverted olefin is recirculated to the epoxidation stage.

The duration of the reaction may vary within wide limits. It depends notably on the washing solvent content of the peroxidised resin, on the concentration of olefin in the solution, on the temperature, on the type of solvent, on the rate of exhaustion of the desired resin and on the reaction pressure when the olefin is gaseous. It is often between 0.01 and 20 hr. Times greater or less than this can also be suitable however.

The epoxidation reaction may be effected in any apparatus known in itself. The peroxidised resin may be put into suspension in the epoxidation solvent in a tank. It may equally be put in a column in which the olefin solution flows into the epoxidation solvent. Other apparatus may equally be suitable. Continuous or discontinuous operation may be used.

The epoxide obtained may be recovered in any way known in itself. The reaction mixture may thus be submitted to series of fractionations, for example by distillation, in order to separate the epoxide which constitutes the reaction product, and in order to recover the unconverted olefin and the epoxidation solvent which can be recycled to the epoxidation reactor.

One process particularly suitable for preparing epoxides according to the process of the invention consists of putting the unperoxidised resin into a column and successively allowing to flow over this resin the aqueous solution of hydrogen peroxide, the washing solvent, and finally the olefin (possibly in solution in the epoxidation solvent) and then recommencing the cycle after a possible washing of the exhausted resin.

Another process suitable for preparing epoxides according to the process of the invention consists of putting the unperoxidised resin into a column and successively allowing to flow over this resin a solution of acid, a solution of hydrogen peroxide, the washing solvent containing water, the olefin (possibly in solution in the epoxidation solvent) and a dilute solution of acid, and then recommencing the cycle.

The process according to the invention can advantageously be effected according to the working diagram represented in the accompanying figure which represents a cyclic process for carrying out the invention in five stages. The five stages take place in the same reactor into which is put the resin over which various reagents and washing agents are successively passed in the order indicated hereafter. Once the cycle has ended, it is recommenced at stage I. The imaginary line R shows the order of succession of the stages to which the resin is submitted. At stage I, which is the acidification stage, the resin is washed using an aqueous solution of concentrated acid such as for example sulphuric acid. The concentration solution is introduced into the reactor via line 1, in which reactor an aqueous solution of dilute acid is collected at the exit of the reactor via line 2. This aqueous solution of dilute acid is fed into an acid reconcentration apparatus 3, out of which are taken water, via line 4 and, via line 1, a concentrated acid solution which is recycled to stage I.

At stage II, which is the peroxidation stage, the resin still kept in the reactor is put in contact with a solution of hydrogen peroxide which is introduced via line 5 in order to assure peroxidation of the carboxylic resin into percarboxylic resin. The solution collected at the exit of the peroxidation stage via line 6 can be fed via line 7 to the acid reconcentration stage 3. If the solution collected in 6 still contains a lot of hydrogen peroxide, it can be recycled via line 8 to the line 5 which introduces the hydrogen peroxide to the peroxidation stage.

At stage III, which is the washing stage according to the invention, the percarboxylic resin is washed according to the process of the invention by water, alone or in mixture with other suitable solvents. The water-based solvent is introduced via line 9 and a dilute solution containing dilute acid is collected at the exit of stage III via line 10.

At stage IV, which is the epoxidation stage, the olefin to be epoxidised is introduced via line 23 in a mixer 15 which is fed with a solvent of the epoxidation reaction by line 14. The mixture obtained is fed by line 11 to stage IV. The solution collected at the exit of stage IV via line 12 contains the desired epoxide as well as the reaction solvent, residual water from washing of stage III and possibly the unconverted olefin. This solution is fed into 13 where there are effected the separations: via line 16 of water, which is collected in 18; via line 17 of the residual washing water; and via line 14 of the reaction solvent, possibly containing the unconverted olefin.

At stage V, which is the washing stage after epoxidation, the resin is washed in the dilute solution of acid collected in 10 in order to remove the residual propylene and residual epoxidation solvent adsorbed on the resin. The solution collected at the exit of stage V via line 19 and which contains the dilute acid and residual propylene is separated in 20 in order to yield on the one hand an aqueous solution of acid which is fed via line 21 into 3 where acid reconcentration takes place, and on the other hand, a fraction containing the residual propylene and the residual epoxidation solvent which are fed via line 22 to the epoxide separation stage 13.

The epoxides obtained according to the process of the invention are important intermediates in the synthesis of organic products and notably for the preparation of thermosetting resins. It is thus that propylene oxide is used to prepare polyols, themselves used in the preparation of polyurethanes.

In order to illustrate the invention, yet without wishing to limit its scope, examples are given below of how the process is carried out. The apparatus and methods of operation described below can be replaced by equivalents well known to the man in the art.

EXAMPLE 1

The aim of this example is to show the remarkable results obtained during the epoxidation of propylene according to the process of the invention. The tests 7 to 11 were effected according to the process of the invention, whilst tests 1R to 6R were effected by way of comparison.

The method of working is as follows:

1. Peroxidation

A resin of the carboxylic type, brand DUOLITE, grade CC3 (polyacrylic polymer) or C 464 (polycarboxylic polymer) sold by Dia-prosim, is placed in an Erlenmeyer flask. The Erlenmeyer flask is immersed in a thermostatted bath and into it is introduced an oxidising solution containing, per 100 volumes of stabilised 70% hydrogen peroxide, 20 volumes of a 96% aqueous solution of sulphuric acid.

The suspension thus obtained is vigorously agitated with the aid of a blade pyrex agitator in order to keep the resin in suspension.

2. Washing of the Peroxidised Resin

The Erlenmeyer flask is taken out of the bath and its contents poured into a crucible with a frit. The resin is rinsed by pouring a quantity of washing solvent sufficient to easily briefly agitate the resin before the solvent flows through the frit. The operation is repeated 15 to 25 times until acid and oxidising character of the filtrate has almost completely disappeared. In certain cases a subsequent washing using a different solvent was carried out.

The resin is eventually then dried under vacuum.

The active oxygen content of the peroxidised resin is measured by the following test. A quantity of 0.15 g dry resin is taken out and reacted with an excess of potassium iodide in the presence of 2 ml 0.1N sulphuric acid. In order to accelerate the titration this is done in the presence of ammonium molybdate. The iodine liberated is titrated with the aid of 0.1N thiosulphate, the colour change being observed with the aid of VITEX.

3. Epoxidation

Into a 75 ml steel flask are introduced, in the absence of air, the peroxidised resin obtained above (until there is 20 milli-atomgram of active oxygen), 20 ml of dioxane which has been distilled over sodium, and 8.4 g propylene.

The flask is closed, placed in a cradle and immersed in a thermostatted bath where it is continuously agitated. The pressure in the flask is greater than atmospheric pressure. The length of the test is counted as from the time when the flask is immersed.

At the end of the test, the contents of the flask are collected. The resin is filtered, washed and possibly dried. The residual content of active oxygen in the resin is measured as indicated above.

The epoxide is estimated by vapour phase chromatography using apparatus equipped with thermal conductivity filament detectors. Two Inox columns, internal diameter 2.16 mm, with different packing were used. The first, 8 m long, is filled with CHROMOSORB G 80/100 mesh impregnated with 5% Carbowax and enables the substances with 3 carbon atoms to be separated. In this case the column temperature is 92° C., the admission temperature is 180° C. and eluent flow (He) is 15 ml/min. The second column, 2 m long, is filled with unimpregnated CHROMOSORB 101 80/100 mesh, and enables heavy products to be separated. In this case the temperature is programmed from 30° to 220° C., the admission temperature is 150° C. and eluent flow (He) is 10 ml/min.

A potentiometric back-titration enables the epoxide contents obtained by chromotography to be confirmed. This titration is carried out by titrating, with silver nitrate, the excess chloride in the hydrochlorination of the epoxide by a known excess of hydrogen chloride.

On the other hand it has been proved that peroxidised resin does not lose active oxygen in molecular oxygen form in the reaction conditions.

The chromatographic examination enables the epoxide selectivity to be determined; this is defined as the quantity of the epoxide formed in relation to the total quantity of products formed by the epoxidation reaction. The results obtained are summarised in Table I overleaf. These results are confirmed by the potentiometric titration linked to titration of active oxygen at the beginning and the end of the reaction.

TABLE 1

| | | \multicolumn{11}{c}{EPOXIDATION OF PROPYLENE} |
|---|---|---|---|---|---|---|---|---|---|---|---|---|
| No. of test | | 1R | 2R | 3R | 4R | 5R | 6R | 7 | 8 | 9 | 10 | 11 |
| Resin | | CC3 | CC3 | CC3 | CC3 | CC3 | C464 | C464 | C464 | C464 | C464 | CC3 |
| Peroxidation | | | | | | | | | | | | |
| Reagents | | | | | | | | | | | | |
| moist resin | g | 12.06 | 12.06 | 12.01 | 16.97 | 16.97 | 41.03 | 41.03 | 30.03 | 100.06 | | 34.98 |
| wt. of dry matter | g | 7.2 | 7.2 | 7.1 | 10.1 | 10.1 | 19.2 | 19.2 | 14.11 | 47.03 | | 20.53 |
| oxidising soln. | ml | 85 | 85 | 85 | 120 | 120 | 250 | 250 | 182 | 607 | | 247 |
| Temperature | °C | 45 | 45 | 45 | 45 | 45 | 45 | 45 | 45 | 45 | | 45 |
| Duration | h | 3 | 3 | 3 | 3 | 3 | 3 | 3 | 1 | 1 | | 1 |
| Washing after peroxidation | | | | | | | | | | | | |
| washing A solvent | | dioxane | dioxane | CH$_3$OH | CH$_3$OH | dioxane | CH$_3$OH po (2 l) | water* (2 l) | water* (2 l) | water* (2 l) | | water* (2 l) |
| temperature | °C | 22 | 22 | <−10 | <−10 | 22 | <−10 | 22 | 22 | 22 | | 22 |
| washing B solvent | | nil | nil | nil | dioxane (50 ml) | nil | CH$_3$OH po | nil | nil | nil | | nil |
| temperature | 20 C | | | | 22 | | 22 | | | | | |
| Drying after peroxidation | | nil | nil | | | | | | nil | nil | | nil |
| temperature | °C | | | 22 | 22 | 22 | 22 | 22 | | | | |
| duration | h | | | 1 | 20 | 20 | 20 | 20 | | | | |
| Active oxygen content of the resin after peroxidation | milli-at.g/g | 6.65 | 6.65 | 9.4 | 4.55 | 4.55 | 4.95 | 3.55 | 2.9 | 2.7 | | 3.43 |

TABLE 1-continued

| | | EPOXIDATION OF PROPYLENE | | | | | | | | | | |
|---|---|---|---|---|---|---|---|---|---|---|---|---|
| No. of test | | 1R | 2R | 3R | 4R | 5R | 6R | 7 | 8 | 9 | 10 | 11 |
| Resin | | CC3 | CC3 | CC3 | CC3 | CC3 | C464 | C464 | C464 | C464 | C464 | CC3 |
| and washing and possible drying | dry product | | | | | | | | | | | |
| Dry product content | % | | | | | | | 100 | 46.8 | 47 | | ~59 |
| Epoxidation | | | | | | | | | | | | |
| propylene | g | 8.4 | 8.4 | 8.4 | 8.4 | 8.4 | 8.4 | 8.4 | 8.4 | 8.4 | 8.4 | 8.45 |
| dioxane | ml | 20 | 20 | 20 | 20 | 20 | 20 | 20 | 20 | 20 | 20 | 20 |
| temperature | °C | 45 | 45 | 45 | 45 | 45 | 45 | 45 | 45 | 45 | 45 | 45 |
| duration | h | 1 | 16 | 2.5 | 5 | 5 | 26 | 28.5 | 1 | 2 | 4 | 2 |
| Washing after epoxidation | | | | | | | | | | | | |
| Washing C solvent | | dioxane | dioxane | $CH_3OH$ | $CH_3OH$ | dioxane | $CH_3OH$ | $CH_3OH$ | $H_2O$ | $H_2O$ | $H_2O$ | $H_2O$ |
| temperature | °C | 22 | 22 | <−10 | <−10 | 22 | <−10 | <−10 | 22 | 22 | 22 | 22 |
| Washing D solvent | | | | | dioxane (50 ml) | | | | | | | |
| temperature | °C | | | | 22 | | | | | | | |
| Drying after epoxidation | | nil | nil | | | | | | nil | nil | nil | |
| Temperature | °C | | | 22 | 22 | 22 | 22 | 22 | | | | 22 |
| duration | h | | | 1 | 20 | 20 | 20 | 20 | | | | 20 |
| Active oxygen content of the resin after epoxidation washing and possible drying | milli-at.g/ g dry product | 0.3 | <0.05 | 0.35 | 0.4 | 0.35 | 0.3 | 0.1 | 0.88 | 0.295 | 0.45 | 0.305 |
| Selectivity | % | ~0 | ~0 | ~10 | ~15 | ~0 | ~0 | ~100 | ~100 | ~100 | ~100 | ~100 |

*demineralised water

The examination of the results given in the preceding Table I show that washing with water according to the invention allows an excellent conversion rate of active oxygen fixed on the resin into epoxide to be obtained, whereas, if washing is performed with methanol or dioxane, extremely low yields are obtained. In this latter case, a large number of by-products are obtained such as propanediol, acetone, propanal, propanol : . . .

Comparison of test 11 with tests 7, 8, 9 and 10 shows that the nature of the resin has no influence on the selectivity.

EXAMPLE 2

Example 2 is designed to illustrate the development of the formation of epoxypropane. The reaction conditions are those of test 7 given in Table 1. Various samples were taken over a period of time and analysed in order to determine the development of the concentration in epoxide over a period of time. The conversion (quantity of epoxy propane formed in relation to the maximum theoretical value) was measured. The selectivity is about 100%. The results are summarised in Table II below.

TABLE II

| Time (hr) | Conversion (%) |
|---|---|
| 2.5 | 0 |
| 3.5 | 1 |
| 6 | 12 |
| 20.5 | 92 |

The results presented in Table II show that even when the peroxidised resin has been dried, a high epoxide content is obtained in spite of the very long reaction time.

On the other hand, comparison of the results of test 7 presented in Table II with those obtained in tests 8, 9, and 10 given in Table I shows that the reaction rate is greater when the water content of the resin is raised.

EXAMPLE 3

Test 12 below was carried out in order to illustrate the remarkable results obtained when epichlorohydrin is prepared according to the invention.

A peroxy resin such as that used for tests 9 and 10 was used.

It contains 2.55 milli-atomgram of active oxygen per g of dry matter and 67% of dry matter.

A quantity of peroxidised resin is taken corresponding to 20 milli-atomgram of active oxygen and is introduced into a 75 ml steel flask at the same time as 20 ml of dioxane distilled over sodium and 15.6 g of allyl chloride of more than 97% concentration. The temperature is maintained at 45° C. After a reaction for 6 hr 30 min., the epichlorohydrin content is equal to 75% of the theoretical maximum content. No by-product is detected.

EXAMPLE 4

Test 13 below was carried out in order to illustrate the remarkable results obtained when glycidol is prepared according to the invention.

A peroxidised resin such as that used in trials 9 and 10 was used. It contains 4.0 milli-atomgram active oxygen per g of dry matter and 49% dry matter.

A quantity of peroxidised resin is taken corresponding to 20 milli-atomgram active oxygen and is introduced into a round-bottomed flask with a pyrex agitator at the same time as 20 ml demineralised water and 2.32 g allyl alcohol of more than 95% concentration. The temperature is maintained at 45° C. After reaction for 1 hr 45 min the glycidol content is equal to 46% of the maximum theoretical content. No by-product is detected.

EXAMPLE 5

Test 14 was carried out in order to illustrate the remarkable results obtained when 1,2-epoxybutane is prepared according to the invention.

A peroxidised resin such as that used for tests 9 and 10 was used. It contains 2.7 milli-atomgram active oxygen per g of dry matter and about 50% dry matter.

A quantity of peroxidised resin is taken corresponding to 20 milli-atomgram of active oxygen and is introduced into a 75 ml steel flask at the same time as 20 ml dioxane distilled over sodium and 9.76 g butene-1. The temperature is maintained at 45° C. After reaction for 5 hr 30 min the epoxybutane content is near the theoretical maximum content. No by-product is detected.

EXAMPLE 6

Test 15 was carried out to illustrate the remarkable result obtained when 1,2,3,4-diepoxybutane is prepared according to the invention.

A peroxidised resin such as that used in tests 9 and 10 was used. It contains 2.69 milli-atomgram active oxygen per g of the damp material and 92.7% dry matter. The resin thus washed is soaked in dioxane for 15 hr and it is noted that it has not lost any active oxygen.

A quantity of peroxidised resin is taken corresponding to 20 milli-atomgram active oxygen and is introduced into a 75 ml steel flask at the same time as 27 ml dioxane distilled over sodium and 8.5 g butadene. The temperature is maintained at 45° C. After reaction for 1 hr the diepoxybutane content is equal to 92% of the theoretical maximum content.

duced into it an oxidising solution containing sulphuric acid, hydrogen peroxide and water.

The suspension thus obtained is vigorously agitated for 60 minutes with the aid if a blade pyrexagitator in order to maintain the resin in suspension.

Washing the Peroxidised Resin

The resin is dried and washed in water as indicated in Example 1.

In all the cases the resin was washed at 22° C. with a total quantity of water equal to about 2 l.

Epoxidation

In the absence of air, the peroxidised resin obtained above is introduced into a steel flask, together with tetrahydrofuran, propylene and the quantity of water necessary to obtain the desired quantity.

The flask is closed, placed in a cradle and immersed in a thermostatically regulated bath. After a thermostatting period of ¼ hr, the flask is continuously agitated. The duration of the test is counted as from the time the agitation begins.

At the end of the test, the contents of the flask are collected. The resin is filtered and washed. The residual active oxygen content is measured as indicated in example 1. The epoxide is back-titrated potentiometrically.

The results obtained are summarised in Table III overleaf.

TABLE III

| No. of test | | | EPOXIDATION OF PROPYLENE | | | | | | | | |
|---|---|---|---|---|---|---|---|---|---|---|---|
| | | | 16 | 17 | 18 | 19 | 20 | 21 | 22 | 23 | 24 |
| Peroxidation | | | | | | | | | | | |
| Reagents | | | | | | | | | | | |
| Dry resin weight | | g | 4 | 4 | 6 | 6 | 6 | 6 | 6 | 6 | 6 |
| oxidising soln. | | g/g dry resin | | | | | | | | | |
| $H_2O_2$ (100%) | | | 9,1 | 9,1 | 9,1 | 3,9 | 9,1 | 9,1 | 9,1 | 9,1 | 3,9 |
| $H_2SO_4$ (100%) | | | 9,3 | 9,3 | 9,3 | 3,3 | 9,3 | 9,3 | 9,3 | 9,3 | 3,3 |
| water | | | 7,6 | 7,6 | 7,6 | 5,0 | 7,6 | 7,6 | 7,6 | 7,6 | 5,0 |
| Active oxygen content resin after peroxidation and washing | | milli-at.g/g of dry resin | 4,9 | 4,9 | 4,6 | 1,3 | 4,6 | 4,6 | 4,6 | 4,6 | 1,3 |
| Epoxidation | | | | | | | | | | | |
| vol. of reactor reagents and solvents | | ml | 75 | 75 | 75 | 75 | 75 | 75 | 150 | 150 | 75 |
| propylene | | g | 6 | 6 | 19,66 | 19,66 | 19,66 | 19,66 | 19,66 | 19,66 | 19,66 |
| total water | | g | 10,8 | 10,8 | 8,85 | 8,85 | 8,85 | 8,85 | 8,85 | 8,85 | 8,85 |
| dioxane | | mole | 0,465 | — | — | — | — | — | — | — | — |
| tetrahydrofuran | | mole | — | 0,465 | 0,12 | 0,12 | 0,12 | 0,12 | 0,91 | 0,91 | 0,12 |
| temperature | | °C | 40 | 40 | 50 | 50 | 20 | 20 | 50 | 50 | 20 |
| duration | | min. | 60 | 60 | 15 | 15 | 15 | 30 | 30 | 15 | 15 |
| Epoxide yield in relation to active oxygen used. | | % | 98 | 86 | 69 | 74 | 72 | 99 | 93 | 100 | 69 |

EXAMPLE 7

The aim of the example is to show the remarkable results obtained when propylene is epoxidised according to the process of the invention.

The method of working is as follows:

Peroxidation

All the tests were carried out with a resin of the carboxylic type, brand DUOLITE, grade C 464 (polycarboxylic polymer) previously regenerated by washing with a 3N solution of hydrochloric acid, drying at 100° C. and remoistening with demineralised water.

The resin thus treated is placed in an Erlenmeyer flask. The Erlenmeyer flask is immersed in a thermostatically regulated bath kept at 40° C. and there is intro-

EXAMPLE 8

Test 25 was carried out in order to illustrate the remarkable results obtained when 4-[1,2-epoxyethyl]-cyclohexene-1 is prepared.

A resin C464 peroxidised according to the invention is used, prepared as in example 7 (tests 16 to 18 and 20 to 23) and containing 4.88 milli-atomgram active oxygen per g of dry resin and 49% of dry matter.

A quantity of peroxidised resin corresponding to 48 milli-atomgram active oxygen is taken and is introduced into a pyrex round-bottomed flask provided with an agitator at the same time as 18 g of water, 51 g of dioxane and 10 g 4-vinyl cyclohexene-1.

The temperature is maintained at 45° C. After 1 hr of reaction the desired epoxide is obtained in a proportion of 90% in relation to the total quantity of epoxides formed as a mixture with less than 2% 4-vinyl-1,2-epoxycyclohexane, the remainder being constituted of 4-[1,2-epoxyethyl]-1,2-epoxycyclohexane.

EXAMPLE 9

Test 26 was carried out to illustrate the remarkable results obtained when 2,3-epoxybutanediol-1,4 is prepared according to the invention.

A peroxidised resin C464 is used prepared as in example 7 (tests 16 to 18 and 20 to 23) and containing 5.05 milli-atomgram active oxygen per g of dry resin and 41% dry matter.

A quantity of resin is taken corresponding to 44.5 milli-atomgram oxygen and is introduced into a pyrex round-bottomed flask with an agitator at the same time as 52.1 g dioxane and 10.3 g butene -2-diol-1,4.

The temperature is maintained at 45° C. After 20 min the desired epoxide is obtained with a yield in relation to used active oxygen of 100%.

EXAMPLE 10

Test 27 was carried out to illustrate the remarkable results obtained when 1,2-epoxyethylbenzene is prepared according to the invention.

A peroxidised C464 resin is used prepared as in example 7 (tests 16 to 18 and 20 to 23) and containing 4.9 milli-atomgram active oxygen per g of dry matter and 42% of dry matter.

A quantity of resin is taken corresponding to 38 milli-atomgram active oxygen and is introduced into a pyrex round-bottomed flask with an agitator at the same time as 57 g dioxane and 8.3 g styrene.

The temperature is maintained at 20° C. After 5 hr 30 min the desired epoxide is obtained with a yield in relation to used active oxygen of 60%.

We claim:

1. In the preparation of epoxides by reaction of olefins with peroxidised carboxylic resins, the improvement comprising washing the peroxidised carboxylic resins, before said contacting with the olefins, with a washing solvent containing at least 40% by weight of water and up to 60% by weight of a polar solvent, in order to eliminate the solvents, reagents or by-products originating from the preparation of said resins.

2. Process according to claim 1, characterised in that the washing solvent is composed of pure water.

3. Process according to claim 1, characterised in that the washing temperature is between 0° and 80° C.

4. Process according to claim 1, characterised in that the peroxidised carboxylic resin is obtained by reacting a carboxylic resin with a solution of hydrogen peroxide in the presence of an acid.

5. Process according to claim 4, characterised in that the carboxylic resin contains identical or different monomeric units of the formula

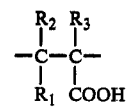

where $R_1$ and $R_3$ represent a hydrogen atom, a halogen atom, a hydroxyl group, a carboxy group, an aryl group substituted or unsubstituted by a halogen, a hydroxyl group or an alkyl group containing 1 to 3 carbon atoms, or an alkyl group substituted or unsubstituted by a halogen, a hydroxyl group or a carboxy group and containing 1 to 5 carbon atoms, $R_1$ and $R_3$ being identical or different and where $R_2$ represents a hydrogen atom or an alkyl group substituted or unsubstituted by a halogen, a hydroxyl group or a carboxy group and containing 1 to 5 carbon atoms.

6. Process according to claim 5, characterised in that the carboxylic resin is chosen amongst polymers, copolymers and graft polymers of acrylic acid and methacrylic acid and hydroxycarboxylated polymers and copolymers.

7. Process according to claim 6, characterised in that the carboxylic resin is a polymer of acrylic acid.

8. Process according to claim 1, applied to the preparation of propylene oxide by reacting propylene.

9. Process according to claim 1, applied to the preparation of epichlorohydrin by reacting allyl chloride.

10. Process according to claim 1, applied to the preparation of glycidol by reacting allyl alcohol.

11. Process according to claim 1, applied to the preparation of butene oxide by reacting butene.

12. Process according to claim 1, applied to the preparation of diopoxybutane by reacting butadiene.

13. Process according to claim 1, applied to the preparation of epoxyethylcyclohexene by reacting vinylcyclohexene.

14. Process according to claim 1, applied to the preparation of 2,3-epoxybutanediol-1,4 by reacting butene-2-diol-1,4.

15. Process according to claim 1, applied to the preparation of epoxyethylbenzene by reacting styrene.

16. Process for preparing epoxides according to claim 1, characterised in that it comprises the following stages:

(1) a carboxylic resin is washed using an acid solution so as to obtain an acidified carboxylic resin, (2) a solution of hydrogen peroxide is passed over the acidified carboxylic resin obtained in 1 so as to obtain a peroxidised carboxylic resin, (3) the peroxidised carboxylic resin obtained in 2 is washed with a solvent containing water so as to obtain a washed peroxidised carboxylic resin, (4) the olefin to be epoxidised is passed over the washed peroxidised carboxylic resin obtained in 3, so as to obtain the desired epoxide and the exhausted carboxylic resin, (5) the exhausted carboxylic resin obtained in 4, is washed using a dilute acid solution so as to recover the carboxylic resin that can be recycled into 1.

* * * * *